United States Patent [19]

Rice et al.

[11] Patent Number: 5,741,138
[45] Date of Patent: Apr. 21, 1998

[54] ORAL COMPOSITIONS

[75] Inventors: David Earl Rice, Cincinnati; Brian Joseph McCormick, Loveland, both of Ohio

[73] Assignee: The Procter & Gamble Company, Cincinnati, Ohio

[21] Appl. No.: 695,486

[22] Filed: Aug. 12, 1996

[51] Int. Cl.$^6$ .................................................. A61C 15/00
[52] U.S. Cl. .................... 433/216; 433/215; 433/228.1
[58] Field of Search ................................. 433/215, 216, 433/228.1

[56] References Cited

U.S. PATENT DOCUMENTS

| | | | |
|---|---|---|---|
| 4,689,223 | 8/1987 | Arias | 424/154 |
| 4,735,945 | 4/1988 | Sakamoto et al. | 514/279 |
| 4,772,470 | 9/1988 | Inone et al. | 424/435 |
| 5,166,233 | 11/1992 | Kuroya et al. | 524/37 |
| 5,227,171 | 7/1993 | Koyama et al. | 424/497 |
| 5,407,921 | 4/1995 | Yoshihisa et al. | 514/75 |

*Primary Examiner*—Nicholas D. Lucchesi
*Attorney, Agent, or Firm*—Douglas C. Mohl; Mary Catherine Hentz; Jacobus C. Rasser

[57] ABSTRACT

The present invention relates to oral compositions containing specially prepared herbal materials; in another aspect the compositions contain a water insoluble noncationic antibacterial agent.

2 Claims, No Drawings

ORAL COMPOSITIONS

TECHNICAL FIELD

The present invention relates to oral compositions containing combinations of herbal materials (preferably extracts thereof) or herbal materials mixed with water insoluble noncationic agents, as antiplaque, anticalculus and anticaries agents.

Plaque induced diseases, including periodontitis and gingivitis, are believed to involve anaerobic bacterial infections. Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ions and/or crystal growth inhibition which prevents the calculus from forming and/or breaks down mature calculus by removing calcium.

Triclosan and herbal materials have been disclosed individually for use in oral products to combat plaque and gingivitis.

Although there have been a number of approaches disclosed for combating periodontal disease, caries and calculus, there is still the desire and need to develop improved products possessing such properties.

It is an object of the present invention to provide compositions which deliver antiplaque, antigingivitis, antiperiodontitis, anticaries and anticalculus benefits employing mixtures of noncationic water insoluble materials and extracts of golden thread and/or honeysuckle flowers or mixtures thereof or mixtures of extracts of golden thread and honeysuckle.

It is a further object of the present invention to produce an effective product using a mixture of above-mentioned materials and other antibacterial/antimicrobial agents.

It is still a further object of the present invention to provide effective methods for combating calculus, plaque, caries, gingivitis and periodontitis.

These and other objects will become more clear from the detailed description which follows.

All percentages and ratios used herein are by weight unless otherwise specified. Also all measurements referred to herein are made at 25° C. in the composition or on the pure material unless otherwise specified.

SUMMARY OF THE INVENTION

The present invention embraces an oral composition comprising:

(a) a safe and effective amount of water insoluble, noncationic antibacterial agent or agents; and (b) an agent selected from the group consisting of extracts of golden thread, honeysuckle flowers and mixtures thereof; and (c) an acceptable carrier.

The present invention further encompasses compositions where the water insoluble noncationic agent is not present but an extract of honeysuckle flowers is present or a mixture of the honeysuckle flowers and the extract of golden thread.

The present invention also encompasses a method for retarding development of dental calculus, plaque, caries, gingivitis and periodontitis.

DETAILED DESCRIPTION OF THE INVENTION

The compositions of the present invention comprise water insoluble noncationic and/or specific herbal extract materials.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "acceptable carrier", as used herein, is meant a suitable carrier which can be used to apply the present agent(s) to the oral cavity without undue toxicity, irritation, allergic response and the like, commensurate with a reasonable benefit/risk ratio.

Water Insoluble Noncationic Agents

Given below are examples of antibacterial agents useful in the compositions of the present invention which are water insoluble and noncationic.

Halogenated Diphenyl Ethers

2',4,4'-trichloro-2-hydroxy-diphenyl ether (Triclosan)
2,2'-dihydroxy-5,5'-dibromo-diphenyl ether.

Phenolic Compounds (including phenol and its homologs, mono- and poly-alkyl and aromatic halophenols, resorcinol and its derivatives, bisphenolic compounds and halogenated salicylanilides).

Phenol and its Homologs

Phenol

| | |
|---|---|
| 2 Methyl | -Phenol |
| 3 Methyl | -Phenol |
| 4 Methyl | -Phenol |
| 4 Ethyl | -Phenol |
| 2,4-Dimethyl | -Phenol |
| 2,5-Dimethyl | -Phenol |
| 3,4-Dimethyl | -Phenol |
| 2,6-Dimethyl | -Phenol |
| 4-n-Propyl | -Phenol |
| 4-n-Butyl | -Phenol |
| 4-n-Amyl | -Phenol |
| 4-tert-Amyl | -Phenol |
| 4-n-Hexyl | -Phenol |
| 4-n-Heptyl | -Phenol |

Mono- and Poly-Alkyl and Aromatic Halophenols p-Chlorophenol

| | |
|---|---|
| Methyl | -p-Chlorophenol |
| Ethyl | -p-Chlorophenol |
| n-Propyl | -p-Chlorophenol |
| n-Butyl | -p-Chlorophenol |
| n-Amyl | -p-Chlorophenol |
| sec-Amyl | -p-Chlorophenol |
| n-Hexyl | -p-Chlorophenol |
| Cyclohexyl | -p-Chlorophenol |
| n-Heptyl | -p-Chlorophenol |
| n-Octyl | -p-Chlorophenol | o-Chlorophenol

| | |
|---|---|
| Methyl | -o-Chlorophenol |
| Ethyl | -o-Chlorophenol |
| n-Propyl | -o-Chlorophenol |
| n-Butyl | -o-Chlorophenol |
| n-Amyl | -o-Chlorophenol |
| tert-Amyl | -o-Chlorophenol |
| n-Hexyl | -o-Chlorophenol |
| n-Heptyl | -o-Chlorophenol |
| o-Benzyl | -p-Chlorophenol |
| o-Benxyl-m-methyl | -p-Chlorophenol |
| o-Benzyl-m, m-dimethyl | -p-Chlorophenol |
| o-Phenylethyl | -p-Chlorophenol |
| o-Phenylethyl-m-methyl | -p-Chlorophenol |
| 3-Methyl | -p-Chlorophenol |
| 3,5-Dimethyl | -p-Chlorophenol |
| 6-Ethyl-3-methyl | -p-Chlorophenol |
| 6-n-Propyl-3-methyl | -p-Chlorophenol |
| 6-iso-Propyl-3-methyl | -p-Chlorophenol |
| 2-Ethyl-3,5-dimethyl | -p-Chlorophenol |
| 6-sec-Butyl-3-methyl | -p-Chlorophenol |
| 2-iso-Propyl-3,5-dimethyl | -p-Chlorophenol |
| 6-Diethylmethyl-3-methyl | -p-Chlorophenol |
| 6-iso-Propyl-2-ethyl-3-methyl | -p-Chlorophenol |
| 2-sec-Amyl-3,5-dimethyl | -p-Chlorophenol |
| 2-Diethylmethyl-3,5-dimethyl | -p-Chlorophenol |
| 6-sec-Octyl-3-methyl | -p-Chlorophenol | p-Bromophenol

| | |
|---|---|
| Methyl | -p-Bromophenol |
| Ethyl | -p-Bromophenol |
| n-Propyl | -p-Bromophenol |
| n-Butyl | -p-Bromophenol |
| n-Amyl | -p-Bromophenol |
| sec-Amyl | -p-Bromophenol |
| n-Hexyl | -p-Bromophenol |
| cyclohexyl | -p-Bromophenol | o-Bromophenol

| | |
|---|---|
| tert-Amyl | -o-Bromophenol |
| n-Hexyl | -o-Bromophenol |
| n-Propyl-m,mDimethyl | -o-Bromophenol |
| 2-Phenyl Phenol | |
| 4-Chloro-2-methyl phenol | |
| 4-Chloro-3-methyl phenol | |
| 4-Chloro-3,5-dimethyl phenol | |
| 2,4-dichloro-3,5-dimethylphenol | |
| 3,4,5,6-terabromo-2-methylphenol | |
| 5-methyl-2-pentylphenol | |
| 4-isopropyl-3-methylphenol | |
| 5-Chloro-2-hydroxydiphenylmethane | |

Resorcinol and its Derivatives

Resorcinol

| | |
|---|---|
| Methyl | -Resorcinol |
| Ethyl | -Resorcinol |
| n-Propyl | -Resorcinol |
| n-Butyl | -Resorcinol |
| n-Amyl | -Resorcinol |
| n-Hexyl | -Resorcinol |
| n-Heptyl | -Resorcinol |
| n-Octyl | -Resorcinol |
| n-Nonyl | -Resorcinol |
| Phenyl | -Resorcinol |
| Benzyl | -Resorcinol |
| Phenylethyl | -Resorcinol |
| Phenylpropyl | -Resorcinol |
| p-Chlorobenzyl | -Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |

Bisphenolic Compounds 2,2'-methylene bis(4-chlorophenol)
2,2'-methylene bis(3,4,6-trichlorophenol)
2,2'-methylene bis(4-chloro-6-bromophenol)
bis(2-hydroxy-3,5-dichlorophenyl)sulphide
bis(2-hydroxy-5-chlorobenzyl)sulphide Halogenated Salicylanilides 4',5-dibromosalicylanilide
3,4',5-trichlorosalcylanilide
3,4',5-tribromosalicylanilide
2,3,3',5-tetrachlorosalicylanilide
3,3',5-trichlorosalicylanilide
3,5-dibromo-3'-trifluoromethyl salicylanilide
5-n-octanoyl-3'-trifluoromethyl salicylanilide
3,5-dibromo-4'-trifluoromethyl salicylanilide
3,5-dibromo-3'-trifluoromethyl salicylanilide
(Fluorophene)

Benzoic Esters p-Hydroxybenzoic Acid

| | |
|---|---|
| Methyl | -p-Hydroxybenzoic Acid |
| Ethyl | -p-Hydroxybenzoic Acid |
| Propyl | -p-Hydroxybenzoic Acid |
| Butyl | -p-Hydroxybenzoic Acid |

Halogenated Carbanilides 3,4,4'-trichlorocarbanilide
3-trifluoromethyl-4,4'-dichlorocarbanilide
3,3',4-tichlorocarbanilide The water insoluble noncationic agent, when present, is present in the oral compositions of the present invention in an effective antiplaque amount, typically about 0.01–5% by weight, preferably about 0.03–1%. The agent is substantially water-insoluble, meaning that its solubility is less than about 1% by weight in water at 25° C. and may be even less than about 0.1%. If an ionizable group is present solubility is determined at a pH at which ionization does not occur.

Extracts of Golden Thread and Honeysuckle Flowers

The extracts of herbal materials useful in the development described and claimed herein extracts of honeysuckle flowers, extracts of golden thread, or mixtures thereof. One of the active agents in golden thread is berberine. A reference disclosing berberine is U.S. Pat. No. 5,407,921, Apr. 18, 1995, to Katsuragi et al. incorporated herein by reference in its entirety. Another patent disclosing berberine is U.S. Pat. No. 4,735,945, Apr. 5, 1988, to Sakamoto et al. also incorporated by reference herein in its entirety.

Golden thread and honeysuckle flowers are natural materials and can be obtained from the plants themselves or synthesized if desired. A supplier of these herbal materials is East Earth Herb, Inc., Eugene, Oreg.

Golden thread and honeysuckle flowers can be obtained from a number of different sources. These for berberine include the following:

Many Herbs From Berberis, Nadina, Mahonia, *Thalictrum spp.* and very many others in several different families (Annonaceae, Berberidaceae, Menispermaceae, Papaveraceae, Ranunculaceae, Rutaceae and Zingiberaceae).

Honeysuckle flower substitutes include the following which are all materials which contain chlorogenic acid and/or luteolin flavonoids:

Many Herbs from Capraioliaceae family and spp. in many other families (Leguminosae, Flacourtiaceae, Scrophulariaceae, Euphorbiaceae, Fabaceae, Asteraceae, Cistaceae, Passifloraceae, Heptaceae, Juncaeae, Compositae, Resedaceae, Rubiaceae, Labiatae, Umbelliferae, Loganiaceae, Valerianaceae, Menyanthaceae, Comaceae).

Golden thread and honeysuckle flowers extracts are present in the products of this invention at an effective level, generally at a level of 0.005% to about 25% preferably from about 0.01% to about 10% most preferably of from about 3% to about 5%.

Acceptable Carrier

The carrier for the active component(s) can be any vehicle suitable for use in the oral cavity. Such carriers include the usual components of mouthwashes, toothpastes, tooth powders, prophylaxis pastes, lozenges, gums and the like and are more fully described hereinafter. Dentifrices and mouthwashes are the preferred systems.

In addition to the active agent(s), the present compositions may contain other antiplaque/gingivitis agents such as quaternary ammonium compounds, water, stannous salts and zinc salts. These types of agents are described in U.S. Pat. No. 4,656,031, Apr. 7, 1987 to Lane et al., and U.S. Pat. No. 5,004,597, Apr. 2, 1991 to Majeti et al. All incorporated herein by reference in their entirety.

The abrasive polishing material contemplated for use in the present toothpaste part invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and polyphosphonates. For these reasons they are preferred for use herein.

The silica abrasive polishing materials useful herein, as well as the other abrasives, generally have an average particle size ranging between about 0.1 to 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to dentifrice compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in dentifrices at levels of from about 0.005% to about 2% by weight.

Dentifrice compositions can also contain emulsifying agents. Suitable emulsifying agents are those which are reasonably stable and foam throughout a wide pH range, including nonsoap anionic, nonionic, cationic, zwitterionic and amphoteric organic synthetic detergents. Many of these suitable surfactants are disclosed by Gieske et al. in U.S. Pat. No. 4,051,234, Sep. 27, 1977, incorporated herein by reference.

Water is also present in the toothpastes of this invention. Water employed in the preparation of commercially suitable toothpastes should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers of the type mentioned previously herein, xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.10% to 5.0% by weight of the total composition can be used.

It is also desirable to include some humectant material in a toothpaste to keep it from hardening. Suitable humectants include glycerin, xylitol sorbitol, and other edible polyhydric alcohols at a level of from about 5% to about 70%.

Another preferred embodiment of the present invention is a mouthwash composition. Conventional mouthwash composition components can comprise the carrier for the active agents of the present invention. Mouthwashes generally comprise from about 20:1 to about 2:1 of a water/ethyl alcohol solution and preferably other ingredients such as flavor, sweeteners, humectants and sudsing agents such as those mentioned above for dentifrices. The humectants give a moist feel to the mouth. Generally, on a weight basis the mouthwashes of the invention comprise 0% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably 0.03% to 0.3%) flavoring agent, and the balance water.

Suitable lozenge and chewing gum components are disclosed in U.S. Pat. No. 4,083,955, Apr. 11, 1978 to Grabenstetter et al., incorporated herein by reference in its entirety.

Other optional components useful in the present invention are pyrophosphate salts such as those described in U.S. Pat. No. 4,515,772, May 7, 1985 to Parran et al. incorporated herein by reference.

Another agent which can be used in the present compositions is an alkali metal bicarbonate, such as sodium bicarbonate. These are stable items of commerce and can be used together with a peroxide compound in separate compartments such as disclosed in U.S. Pat. No. 4,849,213 and U.S. Pat. No. 4,528,180, both to Schaeffer, incorporated herein by reference in their entirety.

The pH of the present compositions and/or its pH in the mouth can be any pH which is safe for the mouth's hard and soft tissues. Such pH's are generally from about 3 to about 10, preferably from about 4 to about 8.5.

METHOD OF MANUFACTURE

The carrier compositions of the present invention can be made using methods which are common in the oral products area.

For example, toothpaste compositions may be prepared by mixing part of the humectant and water together and heating to 66°–71° C. The fluoride source, if present, is then added along with the sweetener, the herbal materials are then added followed by the opacifier and the flavor.

The herbal extracts useful in the present inventions can be formed using a variety of processes such as those set forth below:

Preparation of Crude Herbal Material for Extraction
  1. Crude herbal materials are milled into fine powders
    A Fitzmill comminuting mill is alternating used to a Retschmill for specific milling or reduced sizing needs (e.g., coarse grinding or cryogenic milling). Any grinding operation that achieves the respective particle size for extraction is acceptable. Technical reason for milling step is to have a consistently-sized crude herb powder. Crude herb extractibility is a critical function of exposed surface area of crude herb powder to water mass ratio. To eliminate crude herb particle size as a process variable and since the various herbs have different water-holding capability (porosity/absorptivity), a singular particle size is preferred for process control. Depending on the specific type of crude herbs, milling produces a mix of coarse and fine dust particulates.
  2. All milled crude herb powders are mixed in a Ribbon-type blender for five to 120 minutes to provide uniform particle size of crude herbs prior to extraction. Particle size of milled crude herbal powder is consistent following this step. Alternate blenders such as Waring is acceptable. Chaff fines are discarded at this step.

Crude Herbal Material Extractions in Water (Either option is suitable)
  3. a.) Soxhlet option:
    About 1–60 parts of milled crude herbal powder are added to 100–5000 parts (process and/or deionized or equivalent grade) water in a Soxhlet Extractor and then decanted. A Soxhlet extractor is one or more station continuous reflux extractor with internal condenser slowly feeding 4°–100° C. water across the herb for up to 48 hours.
  b.) Ultrasonics option:
    Suitable alternate extraction process for developing this water soluble extract include use of ultrasonic water extraction systems which can provide equivalent quality, depending on the herb, with up to 94% faster process cycles, hydrolysis extracting reactors, fixed bed extracting reactors, desorption extraction columns, and countercurrent extractors. Due to most commercial extraction process limitations, it is normal to have a small amount of particulates in this extract.
  4. Water-extracted herbal liquid is filtered (e.g., 5–100μfilter cartridge, fine screen or cheesecloth) or centrifuged to remove coarse and/or insoluble particulates.
  5. Filtered water-extracted herbal liquid is concentrated, depending on herbal ingredient, up to a 50% soluble solids level. In addition to concentration by evaporation, alternate suitable process to achieve higher concentrations prior to final drying include freeze concentration, partial freeze drying, membrane separation, vacuum distillation and vacuum drying.
  6. Concentrated herbal extract liquids are dried via commercial drying processes. Suitable driers that are used include fluidized bed, vacuum plate, spray, drum-type and flash driers. Drying efficiency is controlled for water content (<10%) and free water considerations ($\leq 0.80$) to achieve shelf-stability. Yield of soluble powder from the drying process is used as key to optimize herb: water mass formula for extraction.
  7. Dried pure solid herbal extract powders are sized and packaged for shipment. A dessicating-materials such as a silica gel or other suitable FDA-approved, drying agent can be used to control relative humidity and to improve shelf-life.
  8. Dried pure solid herbal extract powder is now ready for reconstitution into oral care products.

COMPOSITIONS USE

The present invention in its method aspect involves applying to the oral cavity safe and effective amounts of the compositions. Generally an amount of at least about 5 grams of a mouthwash and at least about 0.5 of a toothpaste or liquid dentifrice.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

Given below is a composition representative of the present invention.

| Component | Weight % |
| --- | --- |
| Sodium Fluoride, USP | 0.321 |
| Sorbitol, LSR | 32.662 |
| Silica, Precipitated | 20.000 |
| RO Water | 15.478 |
| Glycerine, Synthetic | 8.000 |
| Sodium Alkyl Sulfate Soln | 7.500 |
| PEG 300 Carbowax, NG (PEG6) | 6.000 |
| Tetrapotassium pyrophosphate (60% solution) | 4.212 |
| Sodium acid pyrophosphate | 1.386 |
| Tetrasodium Pyrophosphate Anhydrous | 1.353 |
| Flavor | 1.000 |
| Titanium Dioxide, USP (Rutile) | 0.525 |
| Keltrol (Xanthan Gum, Food Grade) | 0.500 |
| Saccharin | 0.470 |
| Triclosan 99% (irgacare MP) | 0.280 |
| Carbopol 956 | 0.250 |
| Honeysuckle Flowers Extract, Pure Solid | 0.025 |
| Golden Thread Extract, Pure Solid | 0.025 |
| Pigment | 0.013 |

| Component | Wt. % | Wt. % | Wt. % | Wt. % | Wt. % | Wt. % |
| --- | --- | --- | --- | --- | --- | --- |
| Sodium Fluoride | 0.321 | 0.321 | 0.243 | 0.321 | 0.321 | 0 |
| Sorbital, LSR | 32.662 | 31.872 | 37.773 | 37.663 | 45.259 | 48.591 |
| Silica, Precipitated | 20.000 | 20.000 | 20.000 | 20.000 | 20.000 | 20.000 |
| RO Water | 15.478 | 15.516 | 13.945 | 13.978 | 10.200 | 13.000 |
| Glycerine, Synthetic | 8.000 | 8.000 | 8.00 | 8.000 | 10.000 | 0 |
| Sodium Alkyl Sulfate Sulfate Soln. | 7.500 | 6.000 | 6.000 | 6.000 | 7.500 | 7.500 |
| PEG 300 Carbowax, NG (PEG 6) | 6.000 | 4.000 | 4.000 | 4.000 | 4.000 | 3.000 |
| Tetrapotassium Pyrophosphate (60% Soln) | 4.212 | 7.367 | 4.212 | 4.212 | 0 | 0 |
| Sodium Acid Pyrophosphate | 1.386 | 1.650 | 1.386 | 1.386 | 0 | 0 |
| Tetrasodium Pyrophosphate | 1.353 | 2.160 | 1.353 | 1.353 | 0 | 0 |
| Flavor | 1.000 | 1.100 | 1.000 | 1.000 | 0.900 | 0.900 |
| Titanium Dioxide, USP (Rutile or Antase 328) | 0.525 | 0.700 | 0.525 | 0.525 | 0.500 | 0.525 |
| Ketrol, (Xanthan Gum, Food Grade) | 0.500 | 0.500 | 0.500 | 0.500 | 0.700 | 0.600 |
| Sodium Saccharin, USP | 0.470 | 0.300 | 0.470 | 0.470 | 0.150 | 0.150 |
| Triclosan 99% (Irgacare MP) | 0.280 | 0.280 | 0.280 | 0.280 | 0 | 0 |
| Carbopol 956 | 0.250 | 0.250 | 0.250 | 0.25 | 0.220 | 0 |
| Honeysuckle Flowers Extract, Pure Solid | 0.025 | 0.025 | 0.025 | 0.025 | 0.025 | 0.025 |
| Golden Thread Extract, Pure Solid | 0.025 | 0.025 | 0.025 | 0.025 | 0.025 | 0.025 |
| Pigment | 0.0125 | 0 | 0.0125 | 0.0125 | 0.200 | 0 |
| Stannous Fluoride | 0 | 0 | 0 | 0 | 0 | 0454 |
| Stannous Chloride | 0 | 0 | 0 | 0 | 0 | 1.65 |
| Sodium Gluconate, USP | 0 | 0 | 0 | 0 | 0 | 2.200 |
| Sodium Hydroxide, 50% Soln | 0 | 0 | 0 | 0 | 0 | 0.800 |
| Hydroxyethyl Cellulose, NF | 0 | 0 | 0 | 0 | 0 | 0.500 |

In the above compositions, the herbs may be varied using levels set forth herein before. Additionally, the compositions may contain other antiplaque/antigingivitis or anticaries components, such as black tea, oolong tea, green tea, quaternary ammonium compounds, and metal salts such as stannous salts and zinc salts. Furthermore, members of the Ericaceae family may be used. Green, oolong, and black teas are members of the general tea family (*Camillia Sinenis*) and may also be used in the compositions of the present invention.

What is claimed is:

1. A method of reducing plaque on the enamel surfaces of a human or lower animal susceptible to plaque or calculus formation by applying to said enamel surfaces a safe and effective amount of an oral composition comprising:

(a) a safe and effective amount of a water insoluble noncationic antibacterial agent;

(b) an agent selected from the group consisting of an extract of honeysuckle flowers, and an extract of golden thread and mixtures thereof, and (c) a carrier suitable for use in the oral cavity.

2. A method of reducing plaque on the enamel surfaces of a human surfaces of a human or lower animal susceptible to plaque or calculus formation by applying to said enamel surfaces a safe and effective amount of a composition comprising:

(a) an effective amount of extract of honeysuckle flowers or a mixture of an extract of honeysuckle flowers and an extract of golden thread; and (b) a carrier acceptable for use in the oral cavity.

* * * * *